(12) United States Patent
Schlein (10) Patent No.: US 8,404,645 B2
(45) Date of Patent: Mar. 26, 2013

(54) STABLE FORMULATIONS OF AMYLIN AND ITS ANALOGUES

(75) Inventor: Morten Schlein, Vaerløse (DK)

(73) Assignee: Novo Nordisk AS, Bagsvaerd (DK)

( * ) Notice: Subject to any disclaimer, the term of this patent is extended or adjusted under 35 U.S.C. 154(b) by 181 days.

(21) Appl. No.: 12/676,970

(22) PCT Filed: Sep. 11, 2008

(86) PCT No.: PCT/EP2008/062035
§ 371 (c)(1),
(2), (4) Date: May 27, 2010

(87) PCT Pub. No.: WO2009/034118
PCT Pub. Date: Mar. 19, 2009

(65) Prior Publication Data
US 2010/0240587 A1  Sep. 23, 2010

Related U.S. Application Data (60) Provisional application No. 60/972,292, filed on Sep. 14, 2007.

(30) Foreign Application Priority Data

Sep. 11, 2007  (EP) ..................................... 07116066

(51) Int. Cl.
*A61K 38/16* (2006.01)

(52) U.S. Cl. .................... 514/21.3; 514/6.8; 424/400

(58) Field of Classification Search ................. 514/21.3, 514/6.8; 424/400
See application file for complete search history.

(56) References Cited

U.S. PATENT DOCUMENTS

| | | | |
|---|---|---|---|
| 6,309,663 B1 * | 10/2001 | Patel et al. | 424/450 |
| 6,720,001 B2 * | 4/2004 | Chen et al. | 424/455 |
| 7,374,779 B2 * | 5/2008 | Chen et al. | 424/451 |
| 2005/0197287 A1 | 9/2005 | Mack et al. | |

FOREIGN PATENT DOCUMENTS

| | | |
|---|---|---|
| EP | 309100 | 3/1989 |
| EP | 1044015 | 10/2000 |
| WO | WO 92/11862 | 7/1992 |
| WO | WO 99/34764 | 7/1999 |
| WO | WO 01/00223 | 1/2001 |
| WO | WO 01/54742 | 8/2001 |
| WO | WO 03/101395 | 12/2003 |
| WO | WO 2004/037168 | 5/2004 |
| WO | 2004/080480 | 9/2004 |
| WO | 2005/048952 A2 | 6/2005 |

OTHER PUBLICATIONS

Young, A., "Physiology and Pharmacology," Academic Press (2005).
Mudaliar et al., Diabetes Care, "Insulin aspart (B28 asp-insulin): a fast-acting analog of human insulin: absorption kinetics and action profile compared with regular human insulin in healthy nondiabetic subjects", vol. 22: pp. 1501-1506, 1999.

* cited by examiner

*Primary Examiner* — David Lukton
(74) *Attorney, Agent, or Firm* — Jianjie Hu (57) ABSTRACT

The invention relates to a soluble pharmaceutical composition for parenteral administration, which comprises an amylin peptide and an anionic surfactant, and methods for treatment of hyperglycemia.

8 Claims, 4 Drawing Sheets

STABLE FORMULATIONS OF AMYLIN AND ITS ANALOGUES

CROSS-REFERENCE TO RELATED APPLICATIONS

This application is a 35 U.S.C. §371 national stage application of International Patent Application PCT/EP2008/062035 (published as WO 2009/034118), filed Sep. 11, 2008, which claimed priority of European Patent Application 07116066.7, filed Sep. 11, 2007; this application further claims priority under 35 U.S.C. §119 of U.S. Provisional Application 60/972,292, filed Sep. 14, 2007.

FIELD OF THE INVENTION

The invention relates to a soluble pharmaceutical composition for parenteral administration, which comprises an amylin peptide and an anionic surfactant. Methods for treatment of hyperglycemia are also described.

BACKGROUND OF THE INVENTION

Diabetes mellitus is a metabolic disorder in which the ability to utilize glucose is partly or completely lost.

In the treatment of diabetes mellitus, many varieties of insulin formulations. Normally, insulin formulations are administered by subcutaneous injection.

Another peptide of interest in the treatment of diabetes is amylin. The actions of amylin in relation to diabetes are: Reduction of food-intake leading to lower body-weight, slower gastric emptying, smoothening of post-prandial glucose profiles, and reduction in the excessive diabetic glucagon release (A. Young, Amylin: Physiology and Pharmacology, Academic Press (2005)). By and large the actions of amylin are mediated via identified CNS receptors rather than directly on the target organs.

Human amylin is a 37 amino acid long peptide which has physico-chemical properties that make its use as a drug troublesome. In particular, it has a tendency to fibrillate ex-vivo and become ineffective due to precipitation. There is currently on the marked a drug product called Symlin® containing an analog of human amylin (pramlintide) where the three amino acids in positions 25, 28 and 29 each are substituted to proline. This improves substantially the fibrillating tendency. However, even pramlintide is difficult to keep in solution at neutral pH and it is therefore provided in an acidic solution i.e. Symlin®. When a drug is administered at acidic pH there is a risk that it will cause local irritation in the patient.

It would be useful to provide a pharmaceutical composition comprising an amylin peptide in a stable solution at physiological pH.

SUMMARY OF THE INVENTION

The invention relates to a soluble pharmaceutical composition for parenteral administration, which comprises an amylin peptide and an anionic surfactant.

The invention also relates to a soluble pharmaceutical composition for parenteral administration, which comprises an amylin peptide and an anionic surfactant which is 1,2-Dimyristoyl-sn-glycero-3-phospho-rac-(1-glycerol) (DMPG).

It is an object of the invention to obtain pharmaceutical compositions which are stable at physiological pH. In one aspect of the invention the pH of the pharmaceutical composition or a reconstituted solution of said pharmaceutical composition is from about pH 4.0 to about pH 9.0.

The invention furthermore relates to a method for treatment of hyperglycemia by administering a pharmaceutical composition according to the invention and to a pharmaceutical composition as defined for use as a medicament.

DEFINITIONS

The term "amylin peptide" as used herein means amylin, an amylin analogue, an amylin derivative or an amylin agonist.

"Amylin" as used herein refers to a human peptide hormone of 37 amino acids referred to as amylin, which is co-secreted with insulin from β-cells of the pancreas. Human amylin has the following amino acid sequence: Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr (SEQ ID NO:1). Thus, the structural formula is Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr-NH$_2$ (SEQ ID NO: 1) with a disulfidebridge between the two Cys residues and an amide group attached to the C-terminal amino acid via a peptide bond. The term also includes variants of amylin as present in, and in isolatable form, other mammalian species. With respect to a naturally occurring amylin compound, the term includes such a compound in an isolated, purified, or other form that is otherwise not found in nature.

An "agonist" of amylin refers to a compound that mimics one or more effects (or activity) of amylin in vitro or in vivo. The effects of amylin include the ability to directly or indirectly interact or bind with one or more receptors that are activated or deactivated by amylin, for example, the receptor binding assay and the soleus muscle assay described in Examples 2 and 3, respectively in WO 2004/037168. Preferably, the amylin agonist is not a calcitonin, which, as used herein, refers to the human peptide hormone calcitonin and species variations of it, such as that of rat, salmon 10 and eel (including aminosuberic eel calcitonin).

Preferred amylin agonists may also be compounds having at least 60, 65, 70, 75, 80, 85, 90, 95, or 99% amino acid sequence identity to SEQ ID NO: 1 and having amylin activity.

Exemplary amylin agonist analogs contemplated in the use of the invention include those described in U.S. Pat. No. 5,686,411, U.S. Pat. Nos. 6,114,304, and 6,410,511, (Amylin Pharmaceuticals Inc), which are herein incorporated by reference in their entirety.

An "analog" or "analogue" or "agonist analog" of amylin refers to a compound that is similar in structure (e.g., derived from the primary amino acid sequence of amylin by substituting one or more natural or unnatural amino acids or peptidomimetics) to amylin and mimics an effect of amylin in vitro or in vivo.

The nomenclature of various amylin analogs useful in the present invention can be used to indicate both the peptide that the sequence is based on and the modifications made to any basic peptide amylin sequence, such as human amylin. An amino acid followed by a number or an amino acid preceded by a superscript number indicates that the named amino acid replaces the amino acid normally present at the amino acid position of the number/superscript number in the basic amino acid sequence. For example "Arg18 Pro25 Pro 28-h-amylin" and "$^{18}$Arg$^{25,28}$Pro-h-amylin" refers to a peptide based on the sequence of "h-amylin" or "human-amylin" having the following substitutions: Arg replacing His at residue 18, Pro replacing Ala at residue 25 and Pro replacing Ser at residue 28. The terms "des-Lys1-h-amylin" and "des-$^1$Lys-h-amylin" refers to a peptide based on the sequence of human amylin, with the first, or N-terminal, amino acid deleted. Amylin analogs useful according to the invention may also include fragments of amylin such as those described in EP 289287, the contents of which are herein incorporated by reference.

Amylin analogs also include amylin having insertions, deletions, and/or substitutions in at least one or more amino acid positions of SEQ ID NO: 1. The number of amino acid insertions, deletions, or substitutions may be at least 1, 2, 3, 4, 5, 6, 10. Insertions or substitutions may be with other natural or unnatural amino acids, synthetic amino acids, peptidomimetics, or other chemical compounds.

Exemplary compounds include, but are not limited to des-Lys1-h-amylin, Pro28-h-amylin, Pro25 Pro28 Pro29-h-amylin, Arg18 Pro25 Pro28-h-amylin, Pro25 Val26 Pro 28 Pro29-h-amylin and Arg18 Pro25 Pro 28-des-Lys1-h-amylin, which all show amylin activity in vivo in treated test animals, (e.g. provoking marked hyperlactemia followed by hyperglycemia). In addition to having activities characteristic of amylin, certain of the preferred compounds of the invention have also been found to possess more desirable solubility and stability characteristics when compared to human amylin.

A "derivative" of amylin refers to an amylin which is chemically modified, e.g. by introducing a side chain in one or more positions of the amylin backbone or by oxidizing or reducing groups of the amino acid residues in the amylin or by converting a free carboxylic group to an ester group or to an amide group. Other derivatives are obtained by acylating a free amino group or a hydroxy group. Examples of amylin derivatives are described in the international patent application WO 2007/104789 (Novo Nordisk A/S) and pending European patent application no. 07116067.5. Further examples of amylin derivatives are N-methylated amylin, such as the amylin peptide described in Yan et al, PNAS, vol. 103, no. 7, p. 2046-2051, 2006, where the amylin is N-methylated in positions 24 and 26.

DESCRIPTION OF THE INVENTION

In one aspect, the invention relates to a soluble pharmaceutical composition for parenteral administration which comprises an amylin peptide and a surfactant.

It is an object of the invention to obtain pharmaceutical compositions which are stable at physiological pH. In one aspect of the invention, the pH of said pharmaceutical composition or a reconstituted solution of said pharmaceutical composition is from about pH 4.0 to about pH 9.0. In a further aspect of the invention, the pH of said pharmaceutical composition or a reconstituted solution of said pharmaceutical composition is from about pH 5.0 to about pH 8.5. In a further aspect of the invention, the pH of said pharmaceutical composition or a reconstituted solution of said pharmaceutical composition is from about pH 6.0 to about pH 8.5. In a further aspect of the invention, the pH of said pharmaceutical composition or a reconstituted solution of said pharmaceutical composition is from about pH 6.5 to about pH 8.5. In a further aspect of the invention, the pH of said pharmaceutical composition or a reconstituted solution of said pharmaceutical composition is from about pH 6.5 to about pH 8.0. In a further aspect of the invention, the pH of said pharmaceutical composition or a reconstituted solution of said pharmaceutical composition is from about pH 7.0 to about pH 8.0. In a further aspect of the invention, the pH of said pharmaceutical composition or a reconstituted solution of said pharmaceutical composition is about pH 7.4.

In another aspect of the invention, the pharmaceutical composition is a solution. In another aspect of the invention, the pharmaceutical composition is a solid. In another aspect of the invention, the pharmaceutical composition is to be reconstituted with an aqueous solution, such as a buffer or water for injection. In another aspect of the invention, the pharmaceutical composition is suitable for administration by injection or infusion. In a further aspect of the invention, the pharmaceutical composition is suitable for administration for subcutaneous administration. In another aspect of the invention, the pharmaceutical composition is suitable for intramuscular administration. In another aspect of the invention, the pharmaceutical composition is suitable for intravenous administration.

In one aspect of the invention, the amylin peptide is amylin, an amylin analogue, an amylin derivative or an amylin agonist.

The amylin peptide of the present invention may be capable of binding to or otherwise directly or indirectly interacting with an amylin receptor, or other receptor or receptors with which amylin itself may interact to elicit a biological response, e.g., reducing food intake. Compounds of the invention may bind an amylin receptor with an affinity of greater than 20 nM, 10 nM, 5 nM, and more preferably with an affinity of greater than 0.10 nM e.g. as determined by the amylin receptor assay in the section "Assays".

Amylin analogs also include amylin having insertions, deletions, and/or substitutions in at least one or more amino acid positions of SEQ ID NO: 1. The number of amino acid insertions, deletions, or substitutions may be at least 1, 2, 3, 4, 5, 6, 10. Insertions or substitutions may be with other natural or unnatural amino acids, synthetic amino acids, peptidomimetics, or other chemical compounds.

In one aspect of the invention, said amylin peptide is human amylin. In one aspect of the invention, said amylin peptide is Pro25 Pro28 Pro29-h-amylin (pramlintide). In a further aspect of the invention, said amylin peptide is human amylin methylated in position 24 and 26.

In one aspect of the invention, the concentration of said amylin peptide is in the range from about 0.05 mg/mL to about 10 mg/mL or from about 0.1 mg/mL to about 4 mg/mL, or from about 0.4 mg/mL to about 1.2 mg/mL.

In one aspect of the invention, the surfactant is an anionic surfactant.

In one aspect of the invention, the pharmaceutical composition comprises an anionic surfactant in a concentration higher than its critical micelle concentration (CMC).

Anionic surfactants may be selected from the group of: Chenodeoxycholic acid, Chenodeoxycholic acid sodium salt, Cholic acid, Dehydrocholic acid, Deoxycholic acid, Deoxycholic acid methyl ester, Digitonin, Digitoxigenin, N,N-Dimethyldodecylamine N-oxide, Docusate sodium, Glycochenodeoxycholic acid sodium, Glycocholic acid hydrate, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine sodium salt, N-Lauroylsarcosine, N-Lauroylsarcosine, Lithium dodecyl sulfate, Lugol, 1-Octanesulfonic acid sodium salt, 1-Octanesulfonic acid sodium salt, Sodium 1-butanesulfonate, Sodium 1-decanesulfonate, Sodium 1-dodecanesulfonate, Sodium 1-heptanesulfonate, Sodium 1-heptanesulfonate, Sodium 1-nonanesulfonate, Sodium 1-propanesulfonate monohydrate, Sodium 2-bromoethanesulfonate, Sodium cholate hydrate, ox or sheep bile, Sodium cholate hydrate, Sodium choleate, Sodium deoxycholate, Sodium dodecyl sulfate, Sodium dodecyl sulfate, Sodium hexanesulfonate, Sodium octyl sulfate, Sodium pentanesulfonate, Sodium taurocholate, Taurochenodeoxycholic acid sodium salt, Taurodeoxycholic acid sodium salt monohydrate, Taurolithocholic acid 3-sulfate disodium salt, Tauroursodeoxycholic acid sodium salt, Trizma® dodecyl sulfate, DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), Dodecylphosphocholine (FOS-Choline-12), Decylphosphocholine (FOS-Choline-10), Nonylphosphocholine (FOS-Choline-9), dipalmitoyl phosphatidic acid, sodium caprylate, and/or Ursodeoxycholic acid.

In one aspect of the invention, the anionic surfactant is a glycerophosphoglycerol derivative. In one aspect of the invention, said glycerophosphoglycerol derivative is a dimyristoyl derivative, e.g. 1,2-Dimyristoyl-sn-glycero-3-phospho-rac-(1-glycerol) (DMPG). In one aspect of the invention, the dimyristoyl derivative is added in a concentration between 0.1 mM and 10 mM, preferably between 0.5 mM and 5 mM, preferably between 0.5 mM and 3 mM. In one aspect of the invention, the dimyristoyl derivative is added in a concentration between 0.1 mM and 0.5 mM. In one aspect of the invention, said glycerophosphoglycerol derivative is 1,2-Dimyristoyl-sn-glycero-3-phospho-rac-(1-glycerol) (DMPG), such as CAS no. 67232-80-8.

In one aspect of the invention, the concentration of said surfactant is from about 5 mg/L to about 50 g/L. In a further aspect of the invention, the concentration of said surfactant is from about 10 mg/L to about 30 g/L. In a further aspect of the invention, the concentration of said surfactant is from about 20 mg/L to about 3000 mg/L. In a further aspect of the invention, the concentration of said surfactant is from about 30 mg/L to about 500 mg/L. In a further aspect of the invention, the concentration of said surfactant is from about 50 mg/L to about 200 mg/L.

In one aspect of the invention, the surfactant is added in a concentration between 0.1 mM and 10 mM, preferably between 0.5 mM and 5 mM, preferably between 0.5 mM and 3 mM.

In one aspect the soluble pharmaceutical composition of the invention comprises a further surfactant. In a further aspect the further surfactant is selected from the group consisting of: Anionic surfactants, non-ionic surfactants, zwitterionic surfactants, cationic surfactants, poloxamers, and alkyl-polyglucosides. In a yet further aspect the further surfactant is selected from the group consisting of: poloxamer 188, poloxamer 407, poloxamer 124, poloxamer 181, poloxamer 182, poloxamer 237, poloxamer 331, poloxamer 338, a polysorbate 20 (Tween-20), a polysorbate 80, a Solutol HS 15, a d-alfa-Tocopheryl polyethylene glycol 1000 succinate, a Tetradecyl-β-D-maltoside and a n-dodecyl β-D-maltoside.

The pharmaceutical compositions of the invention are physically and chemically stable and are soluble at the desired pH. By "soluble at a given pH" is meant that the amylin peptide contained in the composition of the invention is fully dissolved at the pH of the composition where methods for determining whether the amylin peptide contained in the composition of the invention is dissolved are known in the art.

In one aspect, the pharmaceutical composition may be subjected to centrifugation for 20 minutes at 30,000 g and then the amylin peptide concentration in the supernatant may be determined by RP-HPLC. If this concentration is equal within experimental error to the amylin peptide concentration originally used to make the composition, then the amylin peptide is fully soluble in the composition of the invention.

In another aspect, the solubility of the amylin peptide(s) in a composition of the invention can simply be determined by examining by eye the container in which the composition is contained. The amylin peptide(s) is soluble if the solution is clear to the eye and no particulate matter is either suspended or precipitated on the sides/bottom of the container.

In another aspect, the physical stability of the amylin peptide(s) in a composition of the invention can be determined by a ThT fibrillation assay for the assessment of physical stability of protein formulations.

In one aspect of the invention, the pharmaceutical composition according to the invention is a "physical stable" pharmaceutically composition. The term "physical stable" as used in this context means that the amylin peptide does not fibrillate or is lost due to other forms of aggregation, precipitation or adsorption to surfaces, of e.g. the container comprising the pharmaceutical composition. Physical stability may be determined as described in the ThT fibrillation assay under the section "Assays".

Of course, it is to be understood by the skilled artisan that the solubility of the amylin peptide(s) in a composition of the invention may be affected not only by the composition and its pH but also by the temperature and time at which the composition is stored prior to measurement of solubility.

In one aspect of the invention, said pharmaceutical composition comprises a preservative. In one aspect said preservative is selected from the group consisting phenol, m-cresol or a mixture thereof.

In a further aspect of the invention, said pharmaceutical composition comprises a buffer. In one aspect said buffer is selected from the group consisting phosphate, a Good's buffer such as TRIS, BICINE, and HEPES, glycine, glycylglycine, citrate or a mixture thereof. In a further aspect said buffer is selected from the group consisting of: a Good's buffer such as TRIS, BICINE, and HEPES, glycine, glycylglycine or a mixture thereof.

In a further aspect of the invention, said pharmaceutical composition comprises an isotonicity agent. In one aspect, said isotonicity agent is not a salt. In a further aspect, said isotonicity agent is selected from the group consisting of trehalose, glucose, mannitol, sorbitol, glycerol, propylene glycol and a mixture thereof.

In a further aspect of the invention, said pharmaceutical composition comprises a stabiliser. In one aspect, said stabiliser is selected from the group consisting of L-histidine, imidazole and L-arginine. In one aspect, said stabiliser is a polyethylene glycol.

In another aspect, the invention relates to a method for treatment of hyperglycemia by parenteral administration of an effective amount of a pharmaceutical composition, which comprises an amylin peptide, and a surfactant.

In another aspect, the present invention relates to a method for treatment of binge eating or bulimia comprising parenteral administration of an effective amount of a pharmaceutical composition, which comprises an amylin peptide, and a surfactant.

In another aspect, the present invention relates to a method for treatment or prevention of type 2 diabetes, impaired glucose tolerance, type 1 diabetes, obesity, hypertension, syndrome X, dyslipidemia, cognitive disorders, atheroschlerosis, myocardial infarction, coronary heart disease and other cardiovascular disorders, stroke, inflammatory bowel syndrome, dyspepsia and gastric ulcers comprising parenteral administration of an effective amount of a pharmaceutical composition, which comprises an amylin peptide, and a surfactant.

In another aspect, the present invention relates to a method for delaying or preventing disease progression in type 2 diabetes comprising parenteral administration of an effective amount of a pharmaceutical composition, which comprises an amylin peptide, and a surfactant.

In another aspect, the present invention relates to a method for decreasing food intake, decreasing β-cell apoptosis, increasing β-cell function and β-cell mass, and/or for restoring glucose sensitivity to β-cells comprising parenteral administration of an effective amount of a pharmaceutical composition, which comprises an amylin peptide, and a surfactant.

In a further aspect the present invention relates to a method of treating any of the above conditions which further comprises administering to a person in need thereof a pharmaceutically relevant amount of insulin, an insulin analogue, an insulin derivative, GLP-1 or a GLP-1 derivative.

In another aspect, the insulin to be employed in combination with a composition of the present invention refers to is human insulin.

In another aspect, the insulin to be employed in combination with a composition of the present invention refers to is a human insulin analog.

In another aspect, the insulin to be employed in combination with a composition of the present invention refers to is a derivative of a human insulin analog.

In another aspect, the insulin analogs and derivatives are selected from among those disclosed in EP 375437, EP 0 792 290, EP 0 214 826, EP 1660531, EP 1846446, EP 1846447, WO 2007/096431, WO 2007/128817, WO 2007/128815 and EP 0 705 275 (Novo Nordisk A/S), U.S. Pat. No. 5,504,188 and EP 383472 (Eli Lilly) and EP 0 368 187 (Aventis).

In one aspect the insulin derivatives may include insulin glulisine (LysB3 GluB29 human insulin) which is sold under the trade name Apidra® and other insulin derivatives disclosed in U.S. Pat. No. 621,633 (Sanofi Aventis).

In one aspect the insulin derivatives and insulin analogues may include insulin glargine (GlyA21 ArgB31 ArgB32 human insulin) which is a protracted insulin analogue currently marketed as an acidic formulation under the trade name Lantus®. In one aspect the insulin analogue is insulin lyspro (LysB28 ProB29 human insulin) sold under the trade name Humalog® or insulin aspart (AspB28 human insulin) sold under the trade name Novorapid® or Novolog®.

In another aspect the insulin to be employed in combination with a composition of the present invention refers to an insulin molecule which is acylated in one or more positions, such as in the B29 position of human insulin or desB30 human insulin.

In another aspect the insulin to be employed in combination with a composition of the present invention is selected from the group consisting of: GlyA21 ArgB31 ArgB32 human insulin, NεB29-tetradecanoyl GlnB3 des(B30) human insulin), NεB29-tridecanoyl human insulin, NεB29-tetradecanoyl human insulin, NεB29-decanoyl human insulin, DesB30 ArgB31 ArgB32 human insulin, NεB29-dodecanoyl human insulin and LysB29(Nε-hexadecandioyl-γ-Glu)des(B30)humaninsulin.

In another aspect of the invention, the insulin analogs are selected from among those acid stabilised insulin analogs disclosed in WO2004/080480 such as GlyA21 AspB28 desB30 human insulin or GlyA21 GluB28 desB30 human insulin.

In another aspect of the invention, said human insulin analog is human insulin$^{desB30}$ (also known as des(B30) human insulin)

In another aspect the GLP-1 derivative to be employed in combination with a composition of the present invention refers to GLP-1(1-37), exendin-4(1-39), insulinotropic fragments thereof, insulinotropic analogues thereof and insulinotropic derivatives thereof. Insulinotropic fragments of GLP-1(1-37) are insulinotropic peptides for which the entire sequence can be found in the sequence of GLP-1(1-37) and where at least one terminal amino acid has been deleted. Examples of insulinotropic fragments of GLP-1(1-37) are GLP-1(7-37) wherein the amino acid residues in positions 1-6 of GLP-1(1-37) have been deleted, and GLP-1(7-36) where the amino acid residues in position 1-6 and 37 of GLP-1(1-37) have been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogues of GLP-1(1-37) and exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. Examples of insulinotropic analogues of GLP-1(1-37) are e.g. Met8-GLP-1(7-37) wherein the alanine in position 8 has been replaced by methionine and the amino acid residues in position 1 to 6 have been deleted, and Arg34-GLP-1(7-37) wherein the valine in position 34 has been replaced with arginine and the amino acid residues in position 1 to 6 have been deleted. An example of an insulinotropic analogue of exendin-4(1-39) is Ser2Asp3-exendin-4(1-39) wherein the amino acid residues in position 2 and 3 have been replaced with serine and aspartic acid, respectively (this particular analogue also being known in the art as exendin-3). Insulinotropic derivatives of GLP-1(1-37), exendin-4(1-39) and analogues thereof are what the person skilled in the art considers to be derivatives of these peptides, i.e. having at least one substituent which is not present in the parent peptide molecule with the proviso that said derivative either is insulinotropic or is a prodrug of an insulinotropic compound. Examples of substituents are amides, carbohydrates, alkyl groups and lipophilic substituents. Examples of insulinotropic derivatives of GLP-1(1-37), exendin-4(1-39) and analogues thereof are GLP-1(7-36)-amide, Arg34, Lys26(Nε-(γ-Glu(Nα-hexadecanoyl)))-GLP-1(7-37) and Tyr31-exendin-4(1-31)-amide. Further examples of GLP-1(1-37), exendin-4(1-39), insulinotropic fragments thereof, insulinotropic analogues thereof and insulinotropic derivatives thereof are described in WO 98/08871 (Novo Nordisk A/S), WO 99/43706 (Novo Nordisk A/S, U.S. Pat. No. 5,424,286 (Eng), WO 00/09666 (The Government of the USA), WO 2006/097537 (Novo Nordisk A/S) and European Patent application No. 08101008.4 (Novo Nordisk A/S).

When the pharmaceutical compositions according to the present invention are administered by injection, e.g. via a pen or a syringe, it is typically administered 3 times per day, preferably before meals. It is preferred that each administration comprises less than about 500 μL, or less than about 200 μL since larger injection volumes are unpleasant for the patient. When the pharmaceutical compositions according to the present invention are administered by a pump, it is typically administrated continuously or discontinuously such as via at least 10 administrations or more per day.

In one aspect of the invention, the method of treatment comprises administration of an effective amount of the pharmaceutical composition which is from 30 μL/day to about 600 μL/day, such as from about 60 μL/day to about 360 μL/day. In another aspect of the invention the method comprises a pharmaceutical composition for administration by subcutaneous injection. In another aspect of the invention, the method comprises a pharmaceutical composition for administration by a pump. In another aspect of the invention, the method comprises administration by a pump which delivers a discontinuous amount of said pharmaceutical composition. In another aspect of the invention, the method comprises administration by a pump which delivers a discontinuous amount of said pharmaceutical composition wherein said discontinuous administration of said pharmaceutical composition is by a pulse dosing for a period of time which is less than the period between pulses.

In another aspect the present invention, relates to the use of an amylin peptide and a surfactant for the manufacture of a pharmaceutical composition for parenteral administration, which comprises an amylin peptide, and a surfactant. In one aspect of the invention, the use comprises a pharmaceutical composition for administration by subcutaneous injection. In another aspect of the invention, the use comprises a pharmaceutical composition for administration by a pump. In another embodi-ment of the invention, the use comprises administration by a pump which delivers a discon-tinuous amount of said pharmaceutical composition. In another aspect of the invention, the use comprises administration by a pump which delivers a discontinuous amount of said pharmaceutical composition wherein said discontinuous administration of said pharmaceutical composition is by a pulse dosing for a period of time which is less than the period between pulses.

In another aspect, the present invention relates to the use of an amylin peptide and a surfactant for the manufacture of a pharmaceutical composition for the treatment of hyperglycemia by parenteral administration, which composition comprises an amylin peptide and a surfactant.

In another aspect, the present invention relates to pharmaceutical composition according to the invention for use in treatment of hyperglycemia. In another aspect, the present invention relates to the use of an amylin peptide and a surfactant for the manufacture of a pharmaceutical composition for the treatment of binge eating or bulimia.

FURTHER ASPECTS OF THE INVENTION

1. A soluble pharmaceutical composition for parenteral administration, which comprises an amylin peptide, and an anionic surfactant.

2. The pharmaceutical composition as defined in aspect 1, wherein the anionic surfactant is a glycerophosphoglycerol derivative or an anionic phospholipid.

3. The pharmaceutical composition as defined in aspect 1 or 2, wherein the anionic surfactant is a dimyristoyl derivative.

4. The pharmaceutical composition as defined in any one of aspects 1-3, wherein the anionic surfactant is 1,2-Dimyristoyl-sn-glycero-3-phospho-rac-(1-glycerol) (DMPG).

5. The pharmaceutical composition as defined in any one of aspects 1-4, wherein the pH of said pharmaceutical composition or a reconstituted solution of said pharmaceutical composition is from about pH 4.0 to about pH 9.0.

6. The pharmaceutical composition as defined in any one of aspects 1-5, wherein the pH of said pharmaceutical composition or a reconstituted solution of said pharmaceutical composition is from about pH 4.5 to about pH 8.5.

7. The pharmaceutical composition as defined in any one of aspects 1-6, wherein the pH of said pharmaceutical composition or a reconstituted solution of said pharmaceutical composition is from about pH 5.0 to about pH 8.5.

8. The pharmaceutical composition as defined in any one of aspects 1-7, wherein the pH of said pharmaceutical composition or a reconstituted solution of said pharmaceutical composition is from about pH 6.0 to about pH 8.5.

9. The pharmaceutical composition as defined in any one of aspects 1-8, wherein the pH of said pharmaceutical composition or a reconstituted solution of said pharmaceutical composition is from about pH 6.5 to about pH 8.5.

10. The pharmaceutical composition as defined in any one of aspects 1-9, wherein the pH of said pharmaceutical composition or a reconstituted solution of said pharmaceutical composition is from about pH 6.8 to about pH 8.0.

11. The pharmaceutical composition as defined in any one of aspects 1-10, wherein the pH of said pharmaceutical composition or a reconstituted solution of said pharmaceutical composition is from about pH 7.0 to about pH 7.8.

12. The pharmaceutical composition as defined in any one of aspects 1-11, wherein the pH of said pharmaceutical composition or a reconstituted solution of said pharmaceutical composition is from about pH 7.2 to about pH 7.6.

13. The pharmaceutical composition as defined in any one of aspects 1-12, wherein the composition is a solution.

14. The pharmaceutical composition as defined in any one of aspects 1-12, wherein the composition is a solid.

15. The pharmaceutical composition as defined in aspect 14, which is to be reconstituted with an aqueous solution, such as a buffer or water for injection.

16. The pharmaceutical composition as defined in any one of aspects 1-15, which is suitable for administration by injection or infusion.

17. The pharmaceutical composition as defined in any one of aspects 1-16, wherein said amylin peptide is amylin, an amylin analog or an amylin agonist.

18. The pharmaceutical composition as defined in any one of aspects 1-17, wherein said amylin peptide is human amylin.

19. The pharmaceutical composition as defined in any one of aspects 1-17, wherein said amylin peptide is Pro25 Pro28 Pro29 $^{25,28,29}$Pro-h-amylin.

20. The pharmaceutical composition as defined in any one of aspects 1-17, wherein said amylin peptide is human amylin methylated in position 24 and 26.

21. The pharmaceutical composition as defined in any one of aspects 1-17 or 19, wherein said anionic surfactant is DMPG and said amylin peptide is Pro25 Pro28 Pro29 $^{25,28,29}$Pro-h-amylin.

22. The pharmaceutical composition as defined in any one of aspects 1-17 or 20, wherein said anionic surfactant is DMPG and said amylin peptide is human amylin methylated in position 24 and 26.

23. The pharmaceutical composition as defined in any one of aspects 1-18, wherein said anionic surfactant is DMPG and said amylin peptide is human amylin.

24. The pharmaceutical composition as defined in any one of aspects 1-23, wherein the concentration of said amylin peptide is in the range from about 0.05 mg/mL to about 10 mg/mL or from about 0.1 mg/mL to about 4 mg/mL, or from about 0.4 mg/mL to about 1.2 mg/mL.

25. The pharmaceutical composition as defined in any one of aspects 1-24, wherein the concentration of the anion surfactant is in the range from about 0.1 mg/mL to about 4.0 mg/mL or from about 1.0 mg/mL to about 4.0 mg/mL or from about 1.3 mg/mL to about 3.4 mg/mL.

26. The pharmaceutical composition as defined in any one of aspects 1-25, wherein the concentration of the anion surfactant is about 2.1.

27. The pharmaceutical composition as defined in any one of aspects 1-25, wherein the concentration of the anion surfactant is in the range from about 0.1 mg/mL to about 3.4 mg/mL.

28. The pharmaceutical composition as defined in any one of aspects 1-27, wherein the concentration of said amylin peptide is in the range from about 0.05 mg/mL to about 10 mg/mL and the concentration of said anionic surfactant is in the range from about 0.1 mg/mL to about 4.0 mg/mL.

29. The pharmaceutical composition as defined in any one of aspects 1-27, wherein the concentration of said amylin peptide is in the range from about 0.05 mg/mL to about 10 mg/mL and the concentration of said anionic surfactant is in the range from about 1.0 mg/mL to about 4.0 mg/mL 30. The pharmaceutical composition as defined in any one of aspects 1-27, wherein the concentration of said amylin peptide is in the range from about 0.05 mg/mL to about 10 mg/mL and the concentration of said anionic surfactant is in the range from about 1.3 mg/mL to about 3.4 mg/mL 31. The pharmaceutical composition as defined in any of the aspects 1-27, wherein the concentration of said amylin peptide is in the range from about 0.05 mg/mL to about 10 mg/mL and the concentration of said anionic surfactant is about 2.1 mg/mL.

32. The pharmaceutical composition as defined in aspect 21, wherein the concentration of Pro25 Pro28 Pro29 $^{25,28,29}$Pro-h-amylin is in the range from about 0.05 mg/mL to about 10 mg/mL and the concentration of DMPG is in the range from about 0.1 mg/mL to about 4.0 mg/mL.

33. The pharmaceutical composition as defined in aspect 21, wherein the concentration of Pro25 Pro28 Pro29 $^{25,28,29}$Pro-h-amylin is in the range from about 0.05 mg/mL to about 10 mg/mL and the concentration of DMPG is in the range from about 1.0 mg/mL to about 4.0 mg/mL 34. The pharmaceutical composition as defined in aspect 21, wherein the concentration of Pro25 Pro28 Pro29 $^{25,28,29}$Pro-h-amylin is in the range from about 0.05 mg/mL to about 10 mg/mL and the concentration of DMPG is in the range from about 1.3 mg/mL to about 3.4 mg/mL 35. The pharmaceutical composition as defined in aspect 21, wherein the concentration of Pro25 Pro28 Pro29 $^{25,28,29}$Pro-h-amylin is in the range from about 0.05 mg/mL to about 10 mg/mL and the concentration of DMPG is about 2.1.

36. The pharmaceutical composition as defined in aspect 21, wherein the concentration of Pro25 Pro28 Pro29 $^{25,28,29}$Pro-h-amylin is in the range from about 0.1 mg/mL to about 4 mg/mL, and the concentration of DMPG is in the range from about 0.1 mg/mL to about 3.4 mg/mL.

37. The pharmaceutical composition as defined in any one of aspects 1-36, wherein said pharmaceutical composition comprises a preservative.

38. The pharmaceutical composition as defined in any one of aspects 1-37, wherein said preservative is selected from the group consisting of phenol, m-cresol or a mixture thereof.

39. The pharmaceutical composition as defined in any one of aspects 1-38, wherein said pharmaceutical composition comprises a buffer.

40. The pharmaceutical composition as defined in aspect 39, wherein said buffer is selected from the group consisting of phosphate, a Good's buffer such as TRIS, BICINE, and HEPES, glycine, glycylglycine, citrate or a mixture thereof.

41. The pharmaceutical composition as defined in aspect 40, wherein said buffer is selected from the group consisting of TRIS, BICINE, and HEPES, glycine, glycylglycine or a mixture thereof.

42. The pharmaceutical composition as defined in any one of aspects 1-41, wherein said pharmaceutical composition comprises an isotonicity agent.

43. The pharmaceutical composition as defined in aspect 42, wherein said isotonicity agent is not a salt.

44. The pharmaceutical composition as defined in aspect 42, wherein said isotonicity agent is selected from the group consisting of trehalose, glucose, mannitol, sorbitol, glycerol, propylene glycol or a mixture thereof.

45. The pharmaceutical composition as defined in any one of aspects 1-44, wherein said pharmaceutical composition comprises a stabilizer.

46. The pharmaceutical composition as defined in aspect 45, wherein said stabiliser is selected from the group consisting of L-histidine, imidazole and L-arginine.

47. The pharmaceutical composition as defined in aspect 45, wherein said stabiliser is a polyethylene glycol.

48. The pharmaceutical composition as defined in any one of aspects 1-47, which comprises a further surfactant.

49. The pharmaceutical composition as defined in aspect 48, wherein said further surfactant is selected from a group consisting of: anionic surfactants, non-ionic surfactants, zwitterionic surfactants, cationic surfactants, poloxamers, and alkyl-polyglucosides.

50. The pharmaceutical composition as defined in aspect 49, wherein said further surfactant is a poloxamer.

51. The pharmaceutical composition as defined in aspect 49 or 50, wherein said further surfactant is a poloxamer 188.

52. The pharmaceutical composition as defined in aspect 49 or 50, wherein said further surfactant is selected from the group consisting of poloxamer 407, poloxamer 124, poloxamer 181, poloxamer 182, poloxamer 237, poloxamer 331 and poloxamer 338.

53. The pharmaceutical composition as defined in aspect 49, wherein said further surfactant is a polysorbate 20 (Tween-20).

54. The pharmaceutical composition as defined in aspect 49, wherein said further surfactant is a polysorbate 80.

55. The pharmaceutical composition as defined in aspect 49, wherein said further surfactant is a Solutol HS 15.

56. The pharmaceutical composition as defined in aspect 49, wherein said further surfactant is a d-alfa-Tocopheryl polyethylene glycol 1000 succinate.

57. The pharmaceutical composition as defined in aspect 49, wherein said further surfactant a Tetradecyl-β-D-maltoside or n-dodecyl β-D-maltoside.

58. The pharmaceutical composition as defined in any one of aspects 48-57, wherein the concentration of said further surfactant is from about 5 mg/L to about 50 g/L.

59. The pharmaceutical composition as defined in any one of aspects 48-58, wherein the concentration of said further surfactant is from about 50 mg/L to about 200 mg/L.

60. A method for treatment of hyperglycemia comprising parenteral administration of an effective amount of the pharmaceutical composition as defined in any of the aspects 1-59.

61. The method as defined in aspect 60, wherein said effective amount of the pharmaceutical composition is from about 30 µL/day to about 600 µL/day, such as from about 60 µL/day to about 360 µL/day.

62. The method as defined in any one of aspects 60-61, wherein administration is by subcutaneous injection.

63. The method as defined in any one of aspects 60-62, wherein administration is by a pump.

64. The method as defined in any one of aspects 60-63, wherein administration is by a pump which delivers a discontinuous amount of said pharmaceutical composition.

65. The method as defined in aspect 64, wherein said discontinuous administration of said pharmaceutical composition is by a pulse dosing for a period of time which is less than the period of time between pulses.

66. The pharmaceutical composition as defined in any one of aspects 1-59 for use as a medicament.

67. The pharmaceutical composition as defined in aspect 66 for use as a medicament for subcutaneous injection.

68. The pharmaceutical composition as defined in aspect 66 for use as a medicament for administration by a pump.

69. The pharmaceutical composition as defined in aspects 66 or 68 for use as a medicament for administration by a pump which delivers a discontinuous amount of said pharmaceutical composition.

70. The pharmaceutical composition as defined in aspect 66 for use as a medicament for discontinuous administration of said medicament by a pulse dosing for a period of time which is less than the period of time between pulses.

71. The pharmaceutical composition as defined in aspect 66 for use as a medicament in the treatment of hyperglycemia.

72. The pharmaceutical composition as defined in aspect 66 for use as a medicament in the treatment of binge eating or bulimia.

Assays

Luciferase Assay (I)

1. Amylin Assay Outline

It has previously been published (Poyner D R et al 2002, Pharmacological Reviews 54(2) 233-246) that activation of Amylin receptors (coexpression of Calcitonin receptor and receptor activity modifying peptides RAMPs) by Amylin leads to an increase in the intracellular concentration of cAMP. Consequently, transcription is activated at promotors containing multiple copies of the cAMP response element (CRE). It is thus possible to measure Amylin activity by use of a CRE luciferase reporter gene introduced into BHK cells also expressing an Amylin receptor.

2. Construction of an Amylin 3(a)/CRE-luc Cell Line

A BHK570 cell line stably transfected with the human calcitonin receptor (CTa) and a CRE-responsive luciferase reportergene. The cell line was further transfected with RAMP-3, using standard methods. This turns the Calcitonin receptor into an Amylin 3(a) receptor. Methotrexate, Neomycin, and Hygromycin are selection markers for luciferase, the Calcitonin receptor, and RAMP-3, respectively.

3. Amylin Luciferase Assay

To perform activity assays, BHK Amylin 3(a)//CRE-luc cells were seeded in white 96 well culture plates at a density of about 20.000 cells/well. The cells were in 100 µl growth medium (DMEM with 10% FBS, 1% Pen/Strep, 1 mM Na-pyruvate, 250 nM Methotrexate, 500 µg/ml Neomycin, and 400 µg/ml Hygromycin). After incubation overnight at 37° C. and 5% $CO_2$, the growth medium was replaced by 50 µl/well assay medium (DMEM (without phenol red), Glumamax™, 10% FBS, and 10 mM Hepes, pH 7.4). Further, 50 µl/well of standard or sample in assay buffer were added. After 4 hours incubation at 37° C. and 5% $CO_2$, the assay medium with standard or sample were removed and replaced by 100 µl/well PBS. Further, 100 µl/well LucLite™ was added. The plates were sealed and incubated at room temperature for 30 minutes. Finally, luminescence was measured on a TopCounter (Packard) in SPC (single photon counting) mode.

Assay (II) General Introduction to ThT Fibrillation Assays for the Assessment of Physical Stability of Protein Formulations Low physical stability of a peptide may lead to amyloid fibril formation, which is observed as well-ordered, thread-like macromolecular structures in the sample eventually resulting in gel formation. This has traditionally been measured by visual inspection of the sample. However, that kind of measurement is very subjective and depending on the observer. Therefore, the application of a small molecule indicator probe is much more advantageous. Thioflavin T (ThT) is such a probe and has a distinct fluorescence signature when binding to fibrils [Naiki et al. (1989) Anal. Biochem. 177, 244-249; LeVine (1999) Methods. Enzymol. 309, 274-284].

Figure 4:
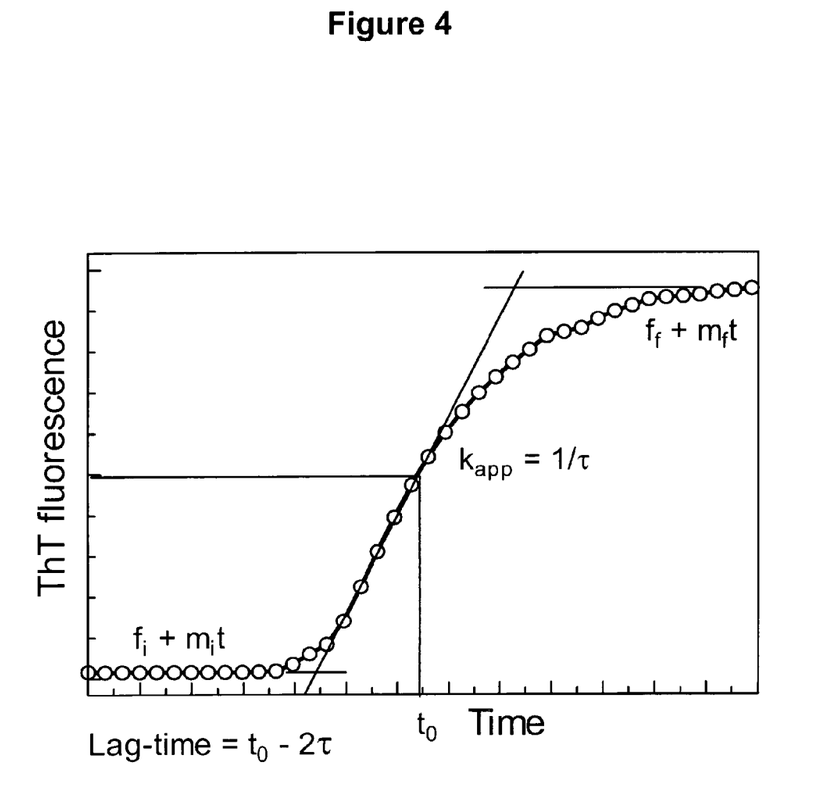
FIG. 4 illustrates the time course for fibril formation.

The time course for fibril formation can be described by a sigmoidal curve with the following expression [Nielsen et al. (2001) Biochemistry 40, 6036-6046]:

$$F = f_i + m_i t + \frac{f_f + m_f t}{1 + e^{-[(t-t_0)/\tau]}} \qquad \text{Eq. (1)}$$

Here, F is the ThT fluorescence at the time t. The constant $t_0$ is the time needed to reach 50% of maximum fluorescence. The two important parameters describing fibril formation are the lag-time calculated by $t_0 - 2\tau$ and the apparent rate constant $k_{app} = 1/\tau$. See FIG. 4.

Formation of a partially folded intermediate of the peptide is suggested as a general initiating mechanism for fibrillation. Few of those intermediates nucleate to form a template onto which further intermediates may assembly and the fibrillation proceeds. The lag-time corresponds to the interval in which the critical mass of nucleus is built up and the apparent rate constant is the rate with which the fibril itself is formed.

Sample Preparation

Samples were prepared freshly before each assay. Each sample composition is described in each example. The pH of the sample was adjusted to the desired value using appropriate amounts of concentrated NaOH and $HClO_4$ or HCl. Thioflavin T was added to the samples from a stock solution in $H_2O$ to a final concentration of 1 µM.

Sample aliquots of 200 µl were placed in a 96 well microtiter plate (Packard Opti-Plate™-96, white polystyrene). Usually, four or eight replica of each sample (corresponding to one test condition) were placed in one column of wells. The plate was sealed with Scotch Pad (Qiagen).

Incubation and Fluorescence Measurement

Incubation at given temperature, shaking and measurement of the ThT fluorescence emission were done in a Fluoroskan Ascent FL fluorescence platereader or Varioskan platereader (Thermo Labsystems). The temperature was adjusted to 37° C. The orbital shaking was adjusted to 960 rpm with an amplitude of 1 mm in all the presented data. Fluorescence measurement was done using excitation through a 444 nm filter and measurement of emission through a 485 nm filter.

Each run was initiated by incubating the plate at the assay temperature for 10 min. The plate was measured every 20 minutes for a desired period of time. Between each measurement, the plate was shaken and heated as described.

Data Handling

The measurement points were saved in Microsoft Excel format for further processing and curve drawing and fitting was performed using GraphPad Prism. The background emission from ThT in the absence of fibrils was negligible. The data points are typically a mean of four or eight samples and shown with standard deviation error bars. Only data obtained in the same experiment (i.e. samples on the same plate) are presented in the same graph ensuring a relative measure of fibrillation between experiments.

The data set may be fitted to Eq. (1). However, since full sigmodial curves in this case are not always achieved during the measurement time, the degree of fibrillation is expressed as ThT fluorescence tabulated as the mean of the samples and shown with the standard deviation at various time points.

Measurement of Initial and Final Concentrations

The peptide concentration in each of the tested formulations were measured both before application in the ThT fibrillation assay ("Initial") and after completion of the ThT fibrillation ("After ThT assay"). Concentrations were determined by reverse HPLC methods using a pramlintide standard as a reference. Before measurement after completion 150 µl was collected from each of the replica and transferred to an Eppendorf tube. These were centrifuged at 30000 G for 40 mins. The supernatants were filtered through a 0.22 µm filter before application on the HPLC system.

EXAMPLES

Example 1

Figure 1:
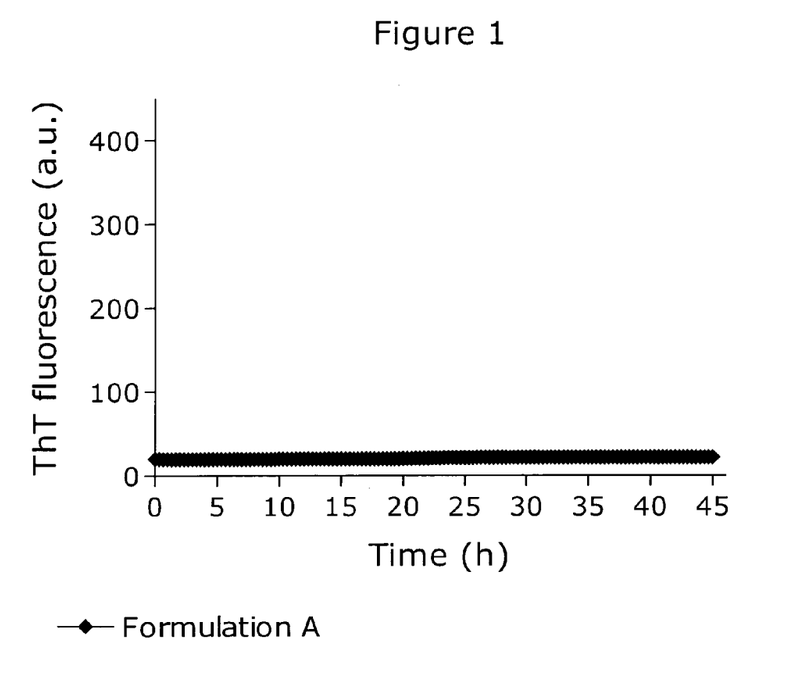
FIG. 1: The physical stability of a pramlintide formulation similar to the commercially available Symlin® formulation as assessed using a ThT fibrillation assay. The figure shows the ThT fluorescence as a function of time.

The physical stability of a pramlintide formulation similar to the commercially available Symlin® formulation was assessed using a ThT fibrillation assay as shown in FIG. 1. Formulation A consisted of 150 µM pramlintide, 4.5 mM sodium acetate, 25.5 mM acetic acid, 236 mM mannitol, 20 mM m-cresol, adjusted to pH 4.0. Under the applied conditions the formulation was inert towards fibrillation as no ThT fluorescence signal emerged.

Example 2

Figure 2:
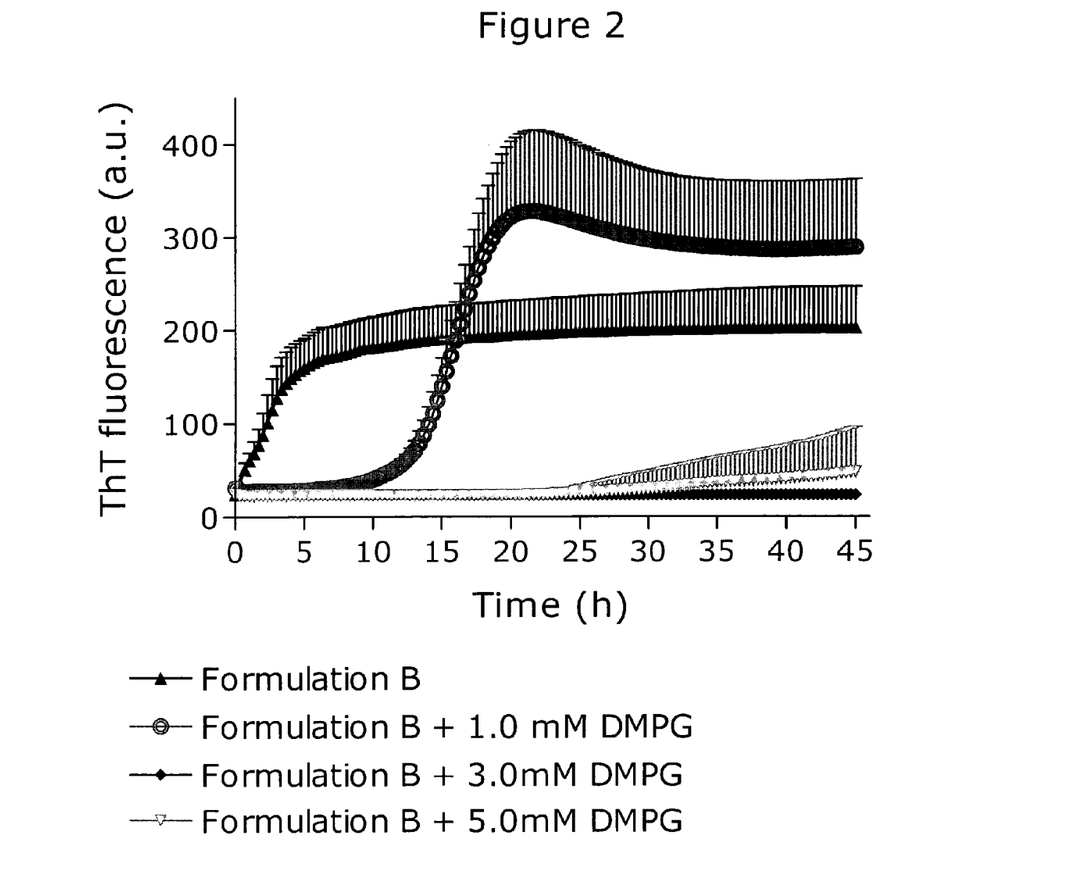
FIG. 2: The physical stability of different pramlintide formulations as assessed using a ThT fibrillation assay. The figure shows the ThT fluorescence as a function of time.

Formulating pramlintide at physiological pH resulted in a physically unstable formulation. This was shown using a ThT fibrillation assay as illustrated in FIG. 2. The ThT fluorescence at certain time points are shown below for the four formulations:

|  | 5 h | SD | 20 h | SD | 40 h | SD |
| --- | --- | --- | --- | --- | --- | --- |
| Formulation B | 159 | 32 | 195 | 37 | 203 | 43 |
| Formulation B + 1.0 mM DMPG | 28 | 0 | 322 | 81 | 287 | 73 |
| Formulation B + 3.0 mM DMPG | 24 | 0 | 23 | 0 | 23 | 0 |
| Formulation B + 5.0 mM DMPG | 23 | 1 | 24 | 2 | 41 | 36 |

Formulation B consisted of 100 µM pramlintide, 174 mM glycerol, 30 mM phenol, 8 mM glycylglycine pH 7.4. This formulation initiated fibrillation almost instantaneously. The addition of 1.0 mM DMPG to formulation B improved the stability and fibrillation initiated after a lag time of approx. 5 hours. Increasing the DMPG concentration to 3.0 mM in formulation B resulted in a formulation inert towards fibrillation as no ThT fluorescence signal emerged during the measurement time. Formulation B with DMPG added to 5.0 mM exhibited a small ThT fluorescence after a lag time of approx. 22 hours, which was significantly longer than formulation B without DMPG.

Example 3

Figure 3:
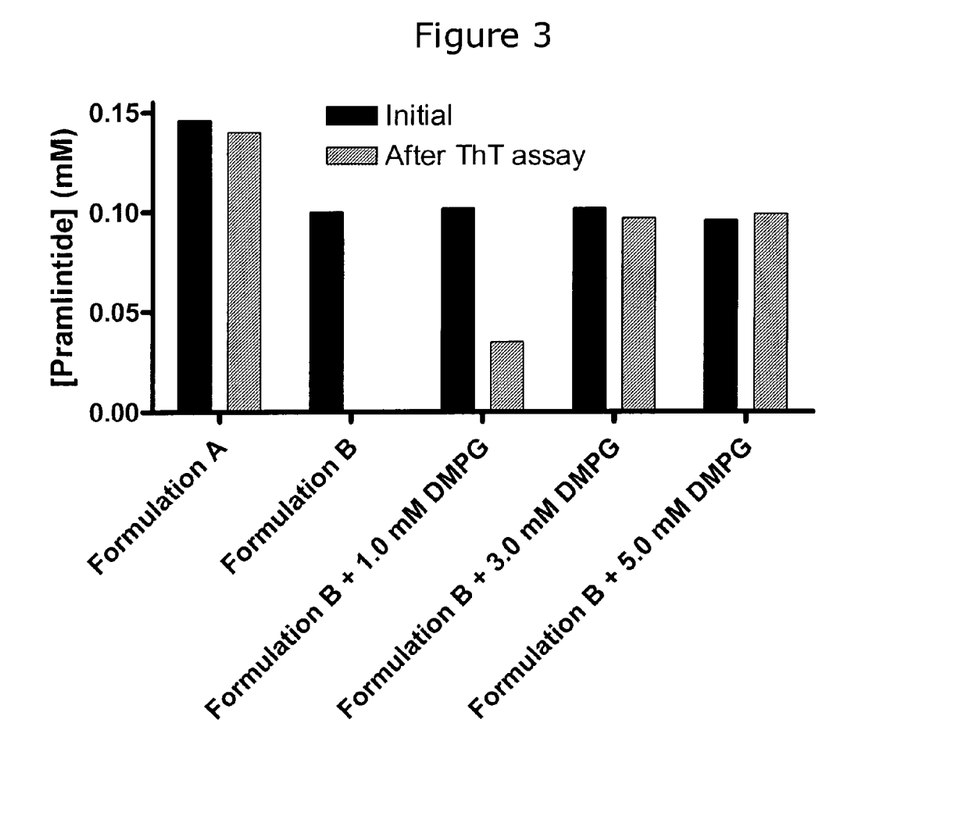
FIG. 3 shows the initial concentration of pramlintide in different pramlintide formulations, and the concentration left in solution after completion of a ThT assay.

The initial concentrations and concentrations of peptide after completion of the ThT fibrillation assay were measured as described above in "Measurement of initial and final concentrations". This was done for Formulation A described in Example 1 and the four Formulation B without and with DMPG as described in Example 2. The results are shown graphically in FIG. 3 and also tabulated below:

|  | Initial conc. (mM) | After ThT assay (mM) |
| --- | --- | --- |
| Formulation A | 0.15 | 0.14 |
| Formulation B | 0.10 | 0.00 |
| Formulation B + 1.0 mM DMPG | 0.10 | 0.04 |
| Formulation B + 3.0 mM DMPG | 0.10 | 0.10 |
| Formulation B + 5.0 mM DMPG | 0.10 | 0.10 |

More than 93% of the pramlintide in Formulation A was recovered after completion of the ThT assay despite the severe stress conditions applied during this assay. Hence, the lag of ThT fluorescence was consisted with a stable pramlintide formulation rather than loss of peptide by adsorption or precipitation or other means.

In Formulation B without DMPG all pramlintide was lost during the ThT assay. Adding DMPG to 1 mM in Formulation B resulted in a recovery of approx. 40% of the initial pramlintide after the ThT fibrillation assay. Increasing the DMPG concentration to 3.0 mM in formulation B resulted in approx. 100% recovery of pramlintide after the assay indicating that the lag of ThT fluorescence was not due to loss of peptide by other means such as adsorption or precipitation. In Formulation B with DMPG added to 5.0 mM approx. 100% of the pramlintide was recovered after the assay despite the very small ThT signal.

The invention claimed is:

1. A soluble pharmaceutical composition for parenteral administration, which comprises an amylin peptide and an anionic phospholipid, and wherein the pH of said pharmaceutical composition or a reconstituted solution of said pharmaceutical composition is from pH 6.0 to pH 8.5.

2. The pharmaceutical composition according to claim 1, wherein the anionic phospholipid is 1,2-Dimyristoyl-sn-glycero-3-phospho-rac-(1-glycerol) (DMPG).

3. The pharmaceutical composition according to claim 1, wherein the composition is a solution.

4. The pharmaceutical composition according to claim 1, wherein said amylin peptide is human amylin, Pro25 Pro28 Pro 29-h-amylin or human amylin methylated in position 24 and 26.

5. The pharmaceutical composition according to claim 1, wherein the concentration of said amylin peptide is in the range from about 0.05 mg/mL to about 10 mg/mL.

6. The pharmaceutical composition according to claim 1, wherein the concentration of the anionic phospholipid is in the range from about 0.1 mg/mL to about 4.0 mg/mL.

7. The pharmaceutical composition according to claim 1, wherein said anionic phospholipid is DMPG and said amylin peptide is Pro25 Pro28 Pro29-h-amylin.

8. A method for treatment of hyperglycemia in a subject in need of such treatment, the method comprising parenteral administration to the subject of a therapeutically effective amount of the pharmaceutical composition according to claim 1.

* * * * *

UNITED STATES PATENT AND TRADEMARK OFFICE
CERTIFICATE OF CORRECTION

| | | |
|---|---|---|
| PATENT NO. | : 8,404,645 B2 | Page 1 of 1 |
| APPLICATION NO. | : 12/676970 | |
| DATED | : March 26, 2013 | |
| INVENTOR(S) | : Morten Schlein | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 258 days.

Signed and Sealed this
Twenty-fourth Day of June, 2014

Michelle K. Lee
*Deputy Director of the United States Patent and Trademark Office*